US006902739B2

(12) United States Patent
McPeak et al.

(10) Patent No.: US 6,902,739 B2
(45) Date of Patent: Jun. 7, 2005

(54) METHODS FOR TREATING JOINT INFLAMMATION, PAIN, AND LOSS OF MOBILITY

(75) Inventors: Patricia McPeak, El Dorado Hills, CA (US); Rukmini Cheruvanky, Folsom, CA (US); Reddy Sastry V. Cherukuri, Folsom, CA (US); Mohammed Mazhar, El Dorado Hills, CA (US)

(73) Assignee: NutraCea, El Dorado Hills, CA (US)

( * ) Notice: Subject to any disclaimer, the term of this patent is extended or adjusted under 35 U.S.C. 154(b) by 0 days.

(21) Appl. No.: 10/012,270

(22) Filed: Nov. 6, 2001

(65) Prior Publication Data

US 2003/0118672 A1 Jun. 26, 2003

Related U.S. Application Data

(60) Provisional application No. 60/307,588, filed on Jul. 23, 2001.

(51) Int. Cl.[7] .............................. A61K 9/48; A61K 9/14
(52) U.S. Cl. ....................... 424/442; 424/400; 424/451; 424/484; 424/489; 424/750; 424/766
(58) Field of Search ................................ 424/442, 400, 424/451, 484, 489, 766, 750, 439

(56) References Cited

U.S. PATENT DOCUMENTS

| 4,129,648 A | * | 12/1978 | Collier et al. ................ 530/392 |
| 4,616,039 A | * | 10/1986 | Herschler .................... 514/711 |
| 5,009,891 A | | 4/1991 | Niwa et al. |
| 5,290,579 A | | 3/1994 | Hitotsumatsu et al. |
| 5,292,537 A | | 3/1994 | Hammond |
| 5,376,390 A | | 12/1994 | Hammond |
| 5,512,307 A | | 4/1996 | Hammond |
| 5,595,982 A | * | 1/1997 | Harless ......................... 514/78 |
| 5,709,855 A | * | 1/1998 | Bockow .................... 424/93.7 |
| 5,753,283 A | | 5/1998 | Hammond |
| 5,916,565 A | | 6/1999 | Rose et al. |
| 5,985,344 A | | 11/1999 | Cherukuri et al. |
| 6,126,943 A | | 10/2000 | Cheruvanky et al. |
| 6,136,851 A | * | 10/2000 | Bonte et al. ................. 514/458 |
| 6,239,171 B1 | * | 5/2001 | Lane et al. .................. 514/458 |
| 6,245,377 B1 | | 6/2001 | Tao |
| 6,303,586 B1 | | 10/2001 | McPeak et al. |
| 6,350,473 B1 | | 2/2002 | Cheruvanky et al. |
| 6,428,817 B1 | * | 8/2002 | Collin ......................... 424/725 |
| 6,432,929 B1 | | 8/2002 | Stone |

FOREIGN PATENT DOCUMENTS

| JP | 61 286317 A | 12/1986 | |
| JP | 61286317 A | * 12/1986 | ............ A61K/7/50 |
| JP | 2001/163796 | 6/2001 | |
| WO | WO 00/56327 | 9/2000 | |

OTHER PUBLICATIONS

Marcella, Kenneth, Exploring the Supplement Jungle, DVM (Jun. 1990; 30, 6).*
Saeedi M., Morteza–Semnani K, Ghoreishi MR.; The treatment of atopic dermatitis with licorice gel; Dermatolog Treat. Sep. 2003; 14(3): 153–7; (Abstract only).
Dalton, L.; What's That Stuff? Licorice; Science & Technology; Aug. 12, 2002; vol. 80, No. 32; CENEAR 80 32, p. 37 ISSN 0009–2347.

* cited by examiner

Primary Examiner—Jyothsan Venkat
(74) Attorney, Agent, or Firm—Townsend and Townsend and Crew LLP

(57) ABSTRACT

This invention provides methods and formulations for treating an inflammatory disease or reducing an inflammatory reaction comprising administering a fortified formulation comprising stabilized rice bran derivative and a fortification agent. Preferred rice bran derivatives are rice bran oil and the solubilized fraction of rice bran. Preferred fortification agents are glucosamine derivative, methylsulfonylmethane, yucca concentrate, and grape seed extract.

11 Claims, 4 Drawing Sheets

METHODS FOR TREATING JOINT INFLAMMATION, PAIN, AND LOSS OF MOBILITY

This application claims priority to U.S. Application Ser. No. 60/307,588, filed Jul. 23, 2001, the disclosure of which is incorporated herein by reference in its entirety for all purposes.

FIELD OF THE INVENTION

This invention relates to fortified formulations and methods for using such formulations for treating joint inflammation, pain, and loss of mobility.

BACKGROUND OF THE INVENTION

Joint disorders and injuries are widespread, can cause considerable discomfort, and cost billions of dollars in lost days of work. Symptoms of these diseases and injuries include inflammation, lameness, loss of mobility, and pain.

Arthritis is a multifactorial degenerative joint disease, which progresses with age and results in joint stiffness, inflammation, and pain. A joint is formed where two bones meet. The healthy joint bones are lined with spongy cartilage which act as shock absorbers, and the synovial fluid, which is secreted by the synovial membrane lining the joint space, acts as a lubricant that prevents friction. There are two major types of arthritis, osteoarthritis, and rheumatoid arthritis.

Osteoarthritis is a condition occurring due to the progressive degeneration and the wearing away of the cartilage (the cushion between the joints), especially at the large joints like the hips and knees. It is a normal age-related degenerative process, occurring gradually after normal wear and tear. Being overweight, inheriting the wrong genes, or simply growing old can make the problem worse. Almost 80% of the people over the age of 60 years, all over the world, suffer from this disorder. OA begins with the breakdown of cartilage resulting in pain, inflammation, and progressive stiffness in the joint. Joint strengthening through exercise, weight maintenance, and non-steroidal anti-inflammatory drugs (NSAIDs) can alleviate symptoms. Osteoarthritis is often accompanied by osteoporosis, a condition where the bone calcium resorption occurs due to hormonal imbalance, making the bone more brittle, which may lead to frequent fractures.

Rheumatoid arthritis is a prostaglandin-mediated joint disease that leads to irreversible crippling of small joints, especially the fingers and toes. This condition is difficult to handle and only prostaglandin synthetase inhibitors can give some relief to patients. Essentially, the body's immune system attacks the cartilage, and the white blood cells (leukocytes) attack the collagen. Statin drugs, which are immunomodulators, are used frequently, though they have serious side effects. Temporary relief may be obtained from NSAIDs. However, overuse of these drugs can lead to ulcers.

Soft tissue rheumatism is a condition where many parts of the body can be affected for a variety of reasons. In many instances, soft tissue rheumatism is a sport-induced injury, such as a sprain, tennis elbow, or runner's knee. Soft tissues are the ligaments, tendons, and tendon sheath. Ligaments are bands of tissue that connect bones. Tendons are bands of tissue that connect muscle to bone. The tendon sheath is the tissue that surrounds and lubricates the tendon. Injury to any of these soft tissues can produce inflammation, pain, and stiffness. These conditions typically clear up quickly, within several days to weeks, and are usually treated with NSAIDs, icing the affected area, and rest. Nevertheless, expedited recovery is still desirable, as these injuries can cause considerable discomfort and reduce workplace productivity.

In addition to the use of NSAIDs, the inflammatory response can be regulated through the use multiple other drugs (see, Goodman & Gilman's "The Pharmacological Basis of Therapeutics" eds. Hardman et al. Ninth Edition, McGraw-Hill Publishing, 1996). Unfortunately, certain anti-inflammatory drugs presently available produce cytotoxic effects that reflect their initial employment as cancer chemotherapeutics, typically anti-neoplastics. For example, corticosteroids, which are often used for treatment of acute inflammation, manifest significant adverse effects, such as inducing Cushingoid features, skin thinning, increased susceptibility to infection, and suppression of the hypothalamic-pituitary-adrenal axis.

Joint injuries and conditions as described above also afflict numerous other mammals, including domesticated animals such as dogs, cats, and horses. In particular, horses often sustain considerable joint injuries due to their participation in sporting events or use for farm work. Lameness due to traumatic joint disease is a common clinical problem in horses and is one of the most important sources of financial losses in the equine industry.

In recent years NSAIDS (non-steroidal anti-inflammatory drugs), such as phenylbutazone, have been used to eliminate, diminish, or at least assist in managing the lameness in performance horses in all aspects of the horse industry (including racing, cutting, reigning, hunter-jumper, dressage, rodeo, barrel-racing). Unfortunately, NSAIDS require prescriptions and/or veterinary dispensing, are costly, and are accompanied by mild severe, and sometimes even catastrophic side effects.

As described previously, such methods for treatment of both humans and animals only allow temporary relief and/or exhibit side effects from prolonged use. Therefore, there is a need for safe and effective treatment which can be used on a long-term basis without side effects and which also promotes rebuilding of the injured/diseased joints. The present invention fulfills this and other needs.

BRIEF SUMMARY OF THE INVENTION

It has now been surprisingly found that a stabilized rice bran derivative, having significant amounts of potent phytonutrients and antioxidants, has an excellent effect in relieving arthritic pain and pain associated with inflammation. Fortification of these derivatives with certain minor herbal components enhances their action. The fortified formulations comprising a stabilized rice bran derivative and a fortification agent reduce inflammation, pain, lameness, and loss of mobility. These fortified formulations are more effective, have more immediate action, and require lower dosages than currently existing formulations for such conditions.

As such, the present invention provides a method for treating an inflammatory disease or reducing an inflammatory reaction in a mammal comprising administering a stabilized rice bran derivative and a fortification agent. The stabilized rice bran derivative can include, but is not limited to rice bran oil, enzyme-treated stabilized rice bran, a solubilized fraction, or mixtures thereof. Preferably, the stabilized rice bran derivative is rice bran oil or the solubilized fraction. The fortification agent can include, but is not limited to, a glucosamine derivative, methylsulfonylmethane, yucca concentrate, or grape seed extract. In preferred embodiments, the administering comprises ingestion of the formulation and the inflammatory disease is a disorder of the bone joint, including, but not limited to, osteoarthritis, osteoporosis, rheumatoid arthritis, and soft tissue rheumatism. The mammal is typically a human or a horse.

In another aspect, the present invention provides a method for treating lameness or loss of mobility in a mammal comprising administration of a formulation comprising a stabilized rice bran derivative and a fortification agent.

In yet another aspect, the present invention provides a method for reducing pain in a mammal, the method comprising administration of a formulation comprising a stabilized rice bran derivative and a fortification agent.

In still yet another aspect, the present invention provides a method for reducing prostaglandin synthetase activity, the method comprising administration of a formulation comprising a stabilized rice bran derivative and a fortification agent.

In another aspect, the invention provides a formulation comprising a stabilized rice bran derivative and fortification agent for treating joint inflammation and loss of mobility. In certain embodiments, the fortification agent is a glucosamine derivative, methylsulfonylmethane, yucca concentrate, or grape seed extract.

Also provided are formulations and methods for treatment of an inflammatory disease, lameness, and loss of mobility comprising administering a tocol composition.

These and other aspects will become more apparent when read with the detailed description and examples, which follow.

Definitions

Unless otherwise specified, the following terms used in the specification and claims have the meanings given below.

The term "fortification agent" refers to any agent which improves the ability of the stabilized rice bran derivative to treat a pathological condition of the joint, such as an inflammatory disease, lameness, loss of mobility, pain. etc. Preferred fortification agents include glucosamine derivatives, methylsulfonylmethane, yucca concentrate, grape seed extract and combinations thereof.

The term "glucosamine derivative" refers to modified versions of glucosamine, such as glucosamine sulfate and N-acetyl glucosamine. These derivatives are the building blocks of proteoglycans, which are used in cartilage synthesis.

The term "methylsulfonylmethane" (MSM) refers to a chemical compound that is a sulfur donor. Depletion of sulfur amino acids leads to arthritis. Sulfur compounds aid in the synthesis of proteoglycans and glucosaminoglycans, which form the basic matrix of cartilage.

The term "yucca concentrate" refers to a preparation of the root of the yucca plant. Yucca is a desert plant that is rich in a steroidal saponin (sarasaponin). This saponin helps the body's production of cortisone and improves the ratio of cortisol/DHEA.

The term "grape seed extract" refers to an extract from grape seeds which has antioxidant effects.

The term "administering" refers to the manner in which a therapeutic agent is introduced to a mammal with a particular condition. Such administration may be by any one of the various standard routes for administration of drugs, i.e., topical, oral (ingestion by the mammal), parenteral, etc.

The term "reducing lameness or loss of mobility" refers to improving the function of any joint. Joint function can be measured by evaluating parameters such as the range of motion and presence of discomfort or pain during movement.

The term "reducing pain in or around a bone joint" refers to alleviating pain localized around a bone joint.

The term "prostaglandin synthetase" (also termed prostaglandin endoperoxide synthase) refers to the cyclooxygenase (COX) enzymes which catalyze the conversion of arachidonic acid to prostanoids.

The term "disorder of the bone joint" refers to any condition where the normal function of the joint, i.e., range of motion, ability to bear weight and the like is impaired, or where use of the joint is accompanied by discomfort or pain. These conditions include those where impairment of the joint is the primary symptom or ones where the disorder has multiple symptoms. These disorders typically affect the bone, joint capsule, cartilage, tendons, ligaments, tendon sheaths, bursa, synovial fluid, etc. Common disorders of the joint include osteoarthritis, rheumatoid arthritis, gout, lupus, tendonitis, bursitis, carpal tunnel syndrome, sprains, etc.

The term "osteoarthritis" refers to a degenerative joint disease where the cartilage that normally cushions the joint and protects it from impact erodes.

The term "rheumatoid arthritis" refers to an autoimmune disease with inflammation of the lining of the joints (synovial membrane). The thickened synovial membrane can erode the surrounding ligaments and bone.

The term "soft tissue rheumatism" refers to conditions where the soft tissues of the body, such as ligaments, tendons, and the tendon sheath are injured.

The term "tocol" refers to E complex vitamins known as tocopherols and tocotrienols which have antioxidant properties. There are at least ten different isomeric forms of these vitamins. The term "tocol composition" refers to any composition comprising tocols.

As used herein the term "enzyme treated stabilized rice bran derivative" refers to an enzyme-treated stabilized rice bran made by mixing a stabilized rice bran with an aqueous solution in a 15% to about a 35% aqueous slurry w/w; adding an enzyme to the aqueous rice bran slurry to convert starch to dextrin, and then directly drying the dextrin solution to form an enzyme treated stabilized rice bran derivative. The enzyme treated stabilized rice bran comprises about 20% to about 30% total dietary fiber.

As used herein the term "GRAS" means generally regarded as safe with respect to food additives.

As used herein the term "stabilized rice bran derivative solubilized fraction" refers to a fraction during a partitioning process. Specifically, after the stabilized rice bran aqueous slurry is enzymatically treated, it is then pumped into a centrifuge where the insoluble fraction precipitates out of the aqueous solution. The aqueous material is pumped to a dryer and then dried. This dried aqueous portion produces the soluble fraction. The constituent parts and their percentages are listed in the Tables below.

DETAILED DESCRIPTION OF THE INVENTION AND PREFERRED EMBODIMENTS

Figure 1:
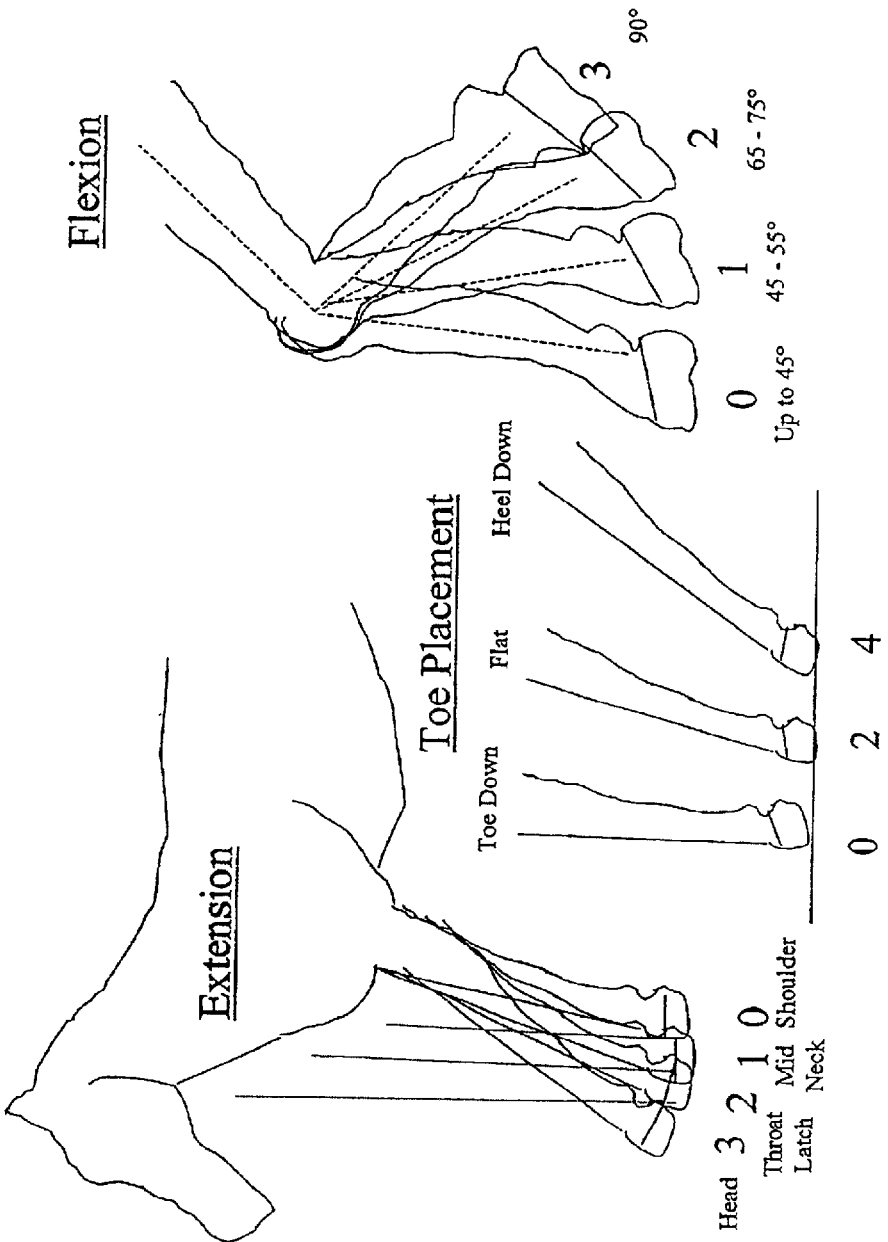
FIG. 1 illustrates the standards used to score the degree of lameness of horses. Horses are evaluated for extension, toe placement, and flexion.

I. Compounds Used in Methods and Formulations of this Invention

Compounds used in formulations and methods of this invention include stabilized rice bran derivatives, which can include, but are not limited to rice bran oil, enzyme-treated stabilized rice bran, a solubilized fraction, or mixtures thereof. Preferably, the stabilized rice bran derivative is rice bran oil or the solubilized fraction. Other compounds used in formulations and methods of this invention include fortification agents which can include, but are not limited to, a glucosamine derivative, methylsulfonylmethane, yucca concentrate, grape seed extract, curcumin, ginger powder, boswellin, aswagandha, and hempseed oil. The compounds of the invention may also comprise an extract of active ingredients of rice bran derivatives, such as tocols.

A. Stabilized Rice Bran Derivatives

In harvested rice, also known as rough rice, the kernel is completely enveloped by the rice hull. The milling process removes the hull, which yields brown rice. The outer brown layer is then removed by an abrasive milling process to generate white rice. The separated brown layer is designated rice bran.

Rice bran is the mesocarp, i.e., the portion between the hull and rice grain, obtained by milling or polishing brown rice. It constitutes about 10% of rough rice. It is generally used as an animal feed. It contains about 18–24% fat, about 25% dietary fiber, about 14% protein and about 45% total carbohydrates besides several potent micronutrients. It is rich in B-complex vitamins, vitamin E and its isomers, minerals like potassium, magnesium, and phosphorous besides several potent antioxidants.

Stabilized rice bran can be commercially purchased or prepared using various methods. Most stabilization methods of rice bran result in inactivation of the lipases which are present, inactivation of the peroxidases, and inactivation of the microorganisms, while still maintaining the high levels of antioxidants in the rice bran. For a general discussion of stabilization and processing see, *Rice Science and Technology*, edited by W. E. Marshall and James I Wadswoth, (1994) pages 390–404.

Stabilized rice bran is available commercially from Producers Rice Mill Inc. (Stuttgart, Ark.), Riceland Foods (Stuttgart, Ark.), Riviana Foods, Inc. (Houston, Tex.), Uncle Ben's Inc. (Houston, Tex.) and The RiceX™ Company (El Dorado Hills, Calif.). Due to different stabilization processes, stabilized rice bran will differ in composition and stabilization characteristics when derived from different manufacturers.

In order to generate the rice bran derivatives for use in the present invention, the rice bran is first stabilized, and then it is further separated into at least two fractions. These include, but are not limited to, a stabilized rice bran soluble derivative and a stabilized rice bran insoluble derivative. Preferably, the separation into the rice bran derivatives includes a nonchemical process i.e., an enzymatic process. In this process, partitioning or fractionation preferably proceeds as outlined hereinafter.

The stabilized rice bran is made into about a 15% to about a 35% slurry, preferably, 20–25% slurry with potable water. An enzyme, which can include, but is not limited to, a dextranase, a maltase, an α-amylase, and various other carbohydrate cleaving enzymes, is added to the batch converting the starch to dextrins. The slurry is heated to about 150° F. to about 200° F. using for instance, a steam injection cooker, a heat exchanger, or other heating method. The slurry is then pumped to a horizontal centrifuge wherein the insoluble fraction is separated. The insoluble fraction is collected and then dried on a belt dryer, and subsequently ground into a powder. This powder is the stabilized rice bran insoluble fraction. The aqueous material is pumped to a drum dryer and then dried. This dried aqueous portion produces the stabilized rice bran solubilized fraction.

The enzyme-treated stabilized rice bran can be generated using the rice bran slurry as described above. The process for making an enzyme-treated stabilized rice bran derivative can comprise admixing stabilized rice bran with an aqueous solution to form about a 15% to about a 35% aqueous rice bran slurry, preferably a 20% to about a 30% aqueous rice bran slurry w/w; adding an enzyme to the aqueous rice bran slurry to convert starch to dextrin, thereby forming an enzyme-treated slurry, and then directly drying the enzyme-treated slurry to form an enzyme-treated stabilized rice bran derivative.

Preferably, after the enzyme is added to the slurry, the slurry is heated to about 150° F. to about 200° F. The slurry is then dried, wherein the drying is accomplished by a process such as belt drying, spray drying, drum drying and air-drying.

These stabilized rice bran derivatives are also available commercially from NutraStar and the RiceX™ Company of California. For the purpose of the invention, stabilized rice bran is available from NutraStar as StaBran™ or from RiceX™ as Stabilized Rice Bran. The soluble derivative is available from NutraStar as RiSolubles™, non-chemically predigested and separated from insoluble fiber, or RiceX™ Ricelin™ from the RiceX™ Company. NutraStar and the RiceX™ Company are located in El Dorado Hills, Calif. Rice bran oil is extracted from rice bran using standard methods known in the art for extracting oils such as peanut oil. The insoluble derivative is available as RiceX™ Fiber Concentrate.

These derivatives have been shown to have more than a hundred (100) potent anti-oxidants. The major antioxidant vitamin E and its isomers known as tocopherols (T) and tocotrienols ($T_3$) are collectively called tocols. A tocol-rich substance is a mixture containing one or more compounds selected from tocopherols (T), tocotrienols ($T_3$), and tocotrienol-like ($T_3$-like) compounds. Stabilized rice bran is the highest natural source of vitamin E.

Antioxidants in stabilized rice bran derivatives include, but are not limited to, γ-oryzanol, β-carotene, several known flavanoids, phytosterols, lipoic acid, and ferulic acid. Some of these compounds are present at a high concentration, much more than in any of the known natural sources.

The processing of rice bran and the nutritional composition of rice bran, as well as other aspects of the stabilized rice bran derivatives used in formulations of this invention, are further described in issued U.S. Pat. No. 6,126,943, entitled "Method for Treating Hypercholesterolemia, Hyperlipidemia, and Atherosclerosis", and allowed U.S. patent application Ser. No. 09/624,474, which are both incorporated herein by reference.

Table I below sets forth the NutraStar StaBran™ Product Data Sheet comprising stabilized Rice Bran and Germ, non-chemically treated to deactivate lipase.

TABLE I

NutraStar StaBran ™ Regular
Product Data Sheet

INGREDIENTS: Stabilized Rice Bran and Germ, non-chemically treated to deactivate Lipase and ensure total stability.

GUARANTEED SPECIFICATIONS:

| | | | |
|---|---|---|---|
| Protein | 12–16% | Soluble Fiber | 2–6% |
| Fat | 18–23% | Ash | 7–10% |
| Total Carbohydrates | 45–55% | Moisture | 4–8% |
| Total Dietary Fiber | 23–35% | Free Fatty Acids | <3% |

TABLE I-continued

NutraStar StaBran ™ Regular Product Data Sheet

| | | | |
|---|---|---|---|
| MICRO- | Total Plate Count | Maximum | 10,000 CFU/g. |
| BIOLOGICAL: | Total Coliform | Maximum | 100 CFU/g. |
| | E. coli | Maximum | <10 CFU/g. |
| | Salmonella | Negative | |
| | Yeast | Maximum | 100 CFU/g. |
| | Mold | Maximum | 100 CFU/g. |
| PHYSICAL: | Appearance | Granular Solid | |
| | Color | Light brown/tan | |
| ¶ | Flavor | Nutty, Toasted | |
| | Bulk Density (g/cc) | 0.47 | |

ANALYTICAL DATA

MACRONUTRIENTS (g/100 g)

| | |
|---|---|
| Protein (N × 6.25) | 14.50 |
| Fat | 20.50 |
| Saturated Fatty Acids | 3.70 |
| Total Carbohydrate | 51.00 |
| Available Carbohydrate | 22.00 |
| Ash | 8.00 |
| Moisture (100 degree vac.) | 6.00 |
| Crude Fiber | 7.30 |
| Total Dietary Fiber | 29.00 |
| Soluble Fiber | 2.00 |
| Calories/100 g. | 330.50 |

VITAMINS
Vitamin A; Carotenoids (mcg/100 g)

| | |
|---|---|
| $\beta$-Carotene | 37.00 |
| $\alpha$-Carotene | 0.40 |
| Lycopene | 2.30 |
| Lutein | 63.80 |
| Zeaxanthin | 18.40 |
| Precryptoxanthin/Cryptoxanthin | 7.40 |
| Total Carotenoids | 129.30 |

Vitamin B Complex (mg/100 g)

| | |
|---|---|
| Vitamin B1 | 2.70 |
| Vitamin B2 | 0.28 |
| Vitamin B3 | 46.90 |
| Vitamin B5 | 3.98 |
| Vitamin B6 | 3.17 |
| Vitamin B12 (mcg/100 g) | <0.500 |
| Vitamin C (mg/100 g) | <0.500 |

Vitamin E Complex (mg/100 g)

| | |
|---|---|
| Tocopherols (T) | 12.00 |
| Tocotrienols (T3) | 13.60 |
| Total Tocols (T + T3) | 25.60 |

Other Micronutrients (mg/100 g)

| | |
|---|---|
| Folic Acid (mcg/100 g) | 26.60 |
| Biotin (mcg/100 g) | 14.10 |
| Choline | 104.80 |
| Inositol | 1496.0 |
| $\gamma$-Oryzanol | 245.15 |

Phytosterols (mg/100 g)

| | |
|---|---|
| $\beta$-Sitosterol | 167.67 |
| Stigmasterol | 62.64 |
| Campesterol | 96.23 |
| Brassicasterol | 14.61 |
| Total Phytosterols | 341.15 |

MINERALS (mg/100 g)

| | |
|---|---|
| Sodium | 8.00 |
| Potassium | 1573.00 |
| Calcium | 40.00 |
| Magnesium | 727.00 |
| Phosphorous | 1591.00 |
| Manganese | 25.60 |
| Iron | 7.70 |
| Copper | 0.27 |
| Zinc | 5.50 |
| Chromium (ppm) | <1 ppm |
| Total Sugars (g/100 g) | 8.09 |
| (No Lactose) | |

Table II below sets forth NutraStar RiSolubles™ product data sheet that comprises stabilized Rice Bran and Germ, non-chemically predigested and separated from insoluble fiber.

TABLE II

NutraStar RiSolubles ™ Product Data Sheet

INGREDIENTS: Stabilized Rice Bran and Germ, non-chemically predigested and separated from insoluble fiber.

GUARANTEED SPECIFICATIONS:

| | | | |
|---|---|---|---|
| Protein | 7–12% | Ash | 3–7% |
| Fat | 25–32% | Moisture | 2–7% |
| Total Carbohydrates | 50–60% | Free Fatty Acids | <3% |
| Total Dietary Fiber | 0–6% | | |

| | | | |
|---|---|---|---|
| MICRO- | Total Plate Count | Maximum | 10,000 CFU/g. |
| BIOLOGICAL: | Total Coliform | Maximum | 100 CFU/g. |
| | E. coli | Maximum | <10 CFU/g. |
| | Salmonella | Negative | |
| | Yeast | Maximum | 100 CFU/g. |
| | Mold | Maximum | 100 CFU/g. |
| PHYSICAL: | Appearance | Fine Powder | |
| | Color | Pale Yellow | |
| | Flavor | Sweet, Nutty | |
| | Bulk Density (G/Cc) | 0.31 | |

ANALYTICAL DATA

MACRONUTRIENTS (g/100 g)

| | |
|---|---|
| Protein (N × 6.25) | 7.50 |
| Fat | 26.50 |
| Saturated Fatty Acid | 4.80 |
| Total Carbohydrate | 57.50 |
| Available Carbohydrate | 54.50 |
| Ash | 5.00 |
| Moisture (100 degree vac.) | 3.00 |
| Crude Fiber | 4.60 |
| Total Dietary Fiber | 3.00 |
| Soluble Fiber | 3.00 |
| Calories/100 g. | 486.50 |

VITAMINS
Vitamin A; Carotenoids (mcg/100 g)

| | |
|---|---|
| $\beta$-Carotene | 8.10 |
| $\alpha$-Carotene | 0.00 |
| Lycopene | 0.20 |
| Lutein | 26.10 |
| Zeaxanthin | 10.90 |
| Precryptoxanthin/Cryptoxanthin | 1.27 |
| Total Carotenoids | 46.57 |

Vitamin B Complex (mg/100 g)

| | |
|---|---|
| Vitamin B1 | 3.60 |
| Vitamin B2 | 0.46 |
| Vitamin B3 | 76.60 |
| Vitamin B5 | 5.82 |
| Vitamin B6 | 5.81 |
| Vitamin B12 (mcg/100 g) | <0.500 |
| Vitamin C (mg/100 g) | <0.500 |

TABLE II-continued

NutraStar RiSolubles ™ Product Data Sheet

| | |
|---|---|
| Vitamin E Complex (mg/100 g) | |
| Tocopherols (T) | 8.00 |
| Tocotrienols (T3) | 10.00 |
| Total Tocols (T + T3) | 18.00 |
| Other Micronutrients (mg/100 g) | |
| Folic Acid (mcg/100 g) | 36.17 |
| Biotin (mcg/100 g) | 14.70 |
| Choline | 150.00 |
| Inositol | 1490.0 |
| γ-Oryzanol | 248.10 |
| Phytosterols (mg/100 g) | |
| β-Sitosterol | 211.90 |
| Stigmasterol | 68.69 |
| Campesterol | 117.32 |
| Brassicasterol | 15.25 |
| Total Phytosterols | 413.16 |
| MINERALS (mg/100 g) | |
| Sodium | 15.75 |
| Potassium | 1562.00 |
| Calcium | 8.30 |
| Magnesium | 170.80 |
| Phosphorous | 763.00 |
| Manganese | 3.20 |
| Iron | 1.90 |
| Copper | 0.07 |
| Zinc | 1.75 |
| Chromium (ppm) | <1 ppm |
| Total Sugars (g/100 g) (No Lactose) | 13.83 |

Table III below sets forth the product data sheet for Rice bran oil.

TABLE III

Rice Bran Oil Refined Product Data Sheet

| Physicochemical Parameters: | | Fatty Acid Profile (%): | |
|---|---|---|---|
| SPECIFICATIONS | | | |
| Appearance | Clear | Myristic Acid (C14:0) | 0.3–0.5 |
| Color (5¼" Lovibond Red) | 3.5 max. | Palmitic Acid (C16:0) | 14.0–20.0 |
| Moisture (%) | 0.05–0.10 | Stearic Acid (C18:0) | 1.2–2.0 |
| Specific gravity @ 25° C. | 0.910–0.920 | Oleic Acid (C18:1) | 40–44 |
| Refractive Index @ 40° C. | 1.460–1.470 | Linoleic (C18:2) | 34–40 |
| Iodine Value | 90–105 | Linolenic (C18:3) | 1.0–2.0 |
| Saponification Value | 180–190 | | |
| Acid Value | <0.5 | Micronutrients: | |
| Unsaponifiables | <3% | Tocopherols & Tocotrienols | 500–600 ppm |
| Smoke Point | ≧213° C./415° F. | | |
| Flash Point | ≧250° C./480° F. | | |
| ANALYSIS | | | |
| Appearance | Clear | Palmitic Acid (C16:0) | 16.0 |
| Color (5¼" Lovibond red) | 3.5 max | Stearic Acid (C18:0) | 2.0 |
| Specific gravity @ 25° C. | 0.916 | Oleic Acid (C18:1) | 42.0 |
| Refractive Index @ 40° C. | 1.47 | Linoleic (C18:2) | 38.0 |
| Smoke Point | 213° C. | Linolenic (C18:3) | 2.0 |
| Iodine Value | 104 | | |
| Saponification Value | 187 | Micronutrients: | |
| Acid Value | <0.5 | Tocopherols & Tocotrienols | 600 ppm |
| Unsaponifiables | <3% | | |

TABLE IV

Antioxidants in NutraStar's Rice Bran Products

Gamma Oryzanol
(2200–3000 ppm)

Gamma Oryzanol is not a single component. It is a mixture of 20 components having different antioxidant properties.
Cycloartenol trans-ferulate
Cycloartenol cis-ferulate
Cycloartanol trans-ferulate
Cycloartanol cis-ferulate
Cycloeucalenol trans-ferulate
Cycloeucalenol cis-ferulate
24-Methylenecycloartanol trans-ferulate
24-Methylenecycloartanol cis-ferulate
24-Methylcholesterol trans-ferulate
24-Methylcholesterol cis-ferulate
β-Sitosterol trans-ferulate
β-Sitosterol cis-ferulate
β-Sitostenol trans-ferulate
β-Sitostenol cis-ferulate
Stigmasterol trans-ferulate
Stigmasterol cis-ferulate
Stigmastenol trans-ferulate
Stigmastenol cis-ferulate
Campesterol trans-ferulate
Campesterol cis-ferulate
Tocopherols & Tocotrienols
(220–320 ppm)

Tocopherols and tocotrienols belong to the same chemical group, but exist in 10 different isomeric forms having different antioxidant properties.
α-Tocopherol
β-Tocopherol
γ-Tocopherol TABLE IV-continued Antioxidants in NutraStar's Rice Bran Products δ-Tocopherol
α-Tocotrienol
β-Tocotrienol
γ-Tocotrienol
δ-Tocotrienol
Desmethyl-tocotrienol
Didesmethyl tocotrienol
Polyphenols Ferulic acid
α-Lipoic acid
Methyl ferulate
ρ-Coumaric acid
ρ-Sinapic acid
Isovitexin
Proanthocyanidins
Metal Chelators Magnesium (6250–8440)
Calcium (303–500)
Phosphorous (14,700–17,000)
Phytosterols
(21 Components)
(2230–4400 ppm)

β-Sitosterol
Campesterol
Stigmasterol
Sitostenol
$\Delta^5$-Avinasterol
$\Delta^7$-Stigmastenol
Sterol glucoside
Acylsterol glucoside
Oligoglycosylsterol
Monoglycosylsterol
Cellotetraosylsitosterol
Methylsterol
Dimethylsterol
Gramisterol
Isofucosterol
Obtusifoliol
Branosterol
28-Homotyphasterol
28-Homosteasteronic acids
6-Deoxycastasterone
β-Amyrin
Carotenoids
(0.9–1.6 ppm)

α-Carotene
β-Carotene
Lycopene
Lutein
Zeaxanthine
Amino Acids

Tryptophan (2100)
Histidine (3800)
Methionine (2500)
Cystein (336–448)
Cystine (336–448)
Arginine (10800)
B Vitamins Thiamin (22–31)
Riboflavin (2.5–3.5)
Niacin (370–660)
Pantothenic acid (36–50)
Pyridoxine (29–42)
Betaine
Dimethyl glycine
Inositol (12000–18,800)
Biotin (0.1–2.2)
Choline (930–1150)
Folic acid (0.20–0.30)
Phytates (1500–1750)

TABLE IV-continued

Antioxidants in NutraStar's Rice Bran Products

Polysaccharides

Cycloartenol-ferulic acid glycoside
Diferulic acid complex
Diferulic acid-calcium complex
Hemicelluloses
Arabinogalactan
Arabinoxylan
Xyloglucan
Proteoglycan
Glycoprotein
Arabinofuranoside
Phospholipids Phosphatidylserine
PhosphatidylCholine
Phosphatidylethanolamine
Lysophophatidylcholine
Lysophosphatidylethanolamine
Enzymes Glutathione peroxidase
Methionine reductase
Superoxide dismutase
Polyphenol oxidase
Catalase
Coenzyme Q10
Aspartate amino transferase isozyme
AAT-1 & AAT-2

B. Fortification Agents

Other compounds used in formulations and methods of this invention include fortification agents which can include, but are not limited to, a glucosamine derivative, methylsulfonylmethane, yucca concentrate, grape seed extract, curcumin, ginger powder, boswellin, aswagandha, and hempseed oil.

Glucosamine sulfate and N-acetylglucosamine can be extracted from crustacean shells. Yucca concentrate is derived from the root of the yucca plant. Methylsulfonylmethane, curcumin, ginger, and boswellin, aswagandha, and hempseed oil are derived from plant sources.

C. Extracts of Active Ingredients of Stabilized Rice Bran

In certain aspects, the active ingredients described above can also be extracted from the stabilized rice bran derivatives and used individually to treating inflammation, pain, lameness, and loss of mobility.

II. Activity of Compounds Used in the Methods and Formulations

The present invention is based on the discovery that rice bran derivatives and extracts of their active ingredients are useful for treating inflammatory reactions, pain, lameness, and loss of mobility. These components seem to act synergistically, creating an enhanced effect not expected when one evaluates the individual compounds present in rice bran derivatives. It is believed that the synergestic activity arises between dense phytonutrients and antioxidants present in the rice bran derivatives.

Without being bound by any particular theory, it is believed that the mechanisms of action of the individual bioactive components in the stability of rice bran derivatives include, but are not limited to, the following:

1. Phytosterols: Beta-sitosterol and its glycosides improve immune function.

2. Gamma-oryzanol acts as an antioxidant and anti-inflammatory agent.

3. Tocotrienols inhibit prostaglandin synthetase activity, which reduces the inflammatory response by suppressing the pro-inflammatory cytokines (IL-4) and elevating the anti-inflammatory cytokines (IL-2).

4. Tocopherols act as antioxidants.

5. Minerals such as magnesium and other trace materials increase absorption of calcium and help in healthy bone mineralization.

6. Proteoglycans, the matrix of collagen, are synthesized from the amino acid pool and polysaccharide units from the rice bran derivative.

7. Polyphenols such as ferulic acid, tocopherols and gamma-oryzanol present in rice bran products are potent anti-oxidants which help in joint function.

8. Omega-3 fatty acids in rice bran products enhance the anti-inflammatory cytokines and inhibit pro-inflammatory cytokines. They are also powerful COX-2 inhibitors.

The invention is further based on the discovery that the administration of stabilized rice bran derivatives with other bioactive compounds are particularly useful for treating inflammatory reactions, pain, lameness, and loss of mobility. Such fortified formulations are more effective, have more immediate action, and require lower dosages than currently existing formulations for such conditions. In certain instances, these components act synergistically, creating an enhanced effect which is greater than the individual compounds acting alone or additively. This synergy is completely unexpected when one evaluates the individual bioactive compounds present in the formulation.

Without being bound by any particular theory, it is believed that the mechanisms of action of these components include, but are not limited to, the following:

1. Yucca concentrate is rich in steroidal saponins, which increases cortisone production. Cortisone has an anti-inflammatory effect.

2. Glucosamine derivatives, such as n-acetyl glucosamine and glucosamine sulfate, promote repair of damaged connective tissues. Specifically, these derivatives promote cartilage production.

3. Methylsulfonylmethane is a sulfur donor for the synthesis of collagen. It maintains the synovial fluid and facilitates the absorption of vitamin C, biotin, and panthothenic acid.

4. Grape seed extract is a potent antioxidant that helps prevent free radical damage at the joints.

5. Curcumin and ginger powder have anti-inflammatory effects.

6. Boswellin is a prostaglandin synthetase inhibitor.

7. Aswagandha is a COX-2 inhibitor.

7. Hempseed oil is rich in omega-3 fatty acids, which have antiinflammatory effects.

Although the mechanism of action of the compounds of the present invention discussed above are believed to be correct, it should in no way be considered as limiting the present invention. Those of skill in the art will understand that the various embodiments of the invention may be practiced regardless of the model used to describe the theoretical underpinnings of the invention.

Animal models that are widely viewed to reflect inflammatory responses and to have predictive value in assessing the efficacy of various treatments for these disorders can be utilized to evaluate the therapeutic efficacy of the compounds described herein. As described in Example 1, the effects of the compounds on joint inflammation and lameness can be assessed in horses with trauma-induced inflammation. Alternatively, improvement of inflammation and mobility can be measured with a collagen-induced rheumatoid arthritis mouse model (see, Enokida M et al. (2001) Bone 28(1): 87–93)

III. Formulation and Dosages Used in Methods of this Invention

The present invention also provides various formulations of stabilized rice bran derivatives and their extracted active ingredients with fortification agents. These formulations include both neutraceutical formulations and standard pharmaceutical compositions.

A. Nutraceuticals

The nutraceutical formulations of this invention can take a variety of forms, such as a powder, a food, a food supplement, a medical food, a liquid, a beverage, an emulsion or mixtures thereof.

To incorporate the fortified formulation of the rice bran derivative into the diet of a mammal various options include, but are not limited to, simply sprinkling the formulation on another food substance (i.e., salad, bread, cereal, etc.), being a major ingredient in a multigrain ready-to-eat cereal, incorporating it into a baked product (breads, muffins, waffles, etc.), pasta, healthy dessert and snacks (athletic bar, healthy drink, etc.) and high fiber foods.

For administration to humans, the fortified formulation of rice bran derivative is preferably a drink, a capsule, or a bar. These formulations typically comprise the solubilized fraction of stabilized rice bran or rice bran oil. Such formulations further comprise a fortification agent which promotes joint health, including, but not limited to, glucosamine derivatives (such as n-acetyl glucosamine, glucosamine sulfate), methylsulfonylmethane, yucca concentrate, and grape seed extract. Additives to improve flavor and consistency of the product are also included in the formulation. Especially preferred formulations and dosages are described in Example 2.

For administration to animals, the fortified formulation of rice bran derivative is a powder or liquid. These formulations typically comprise the solubilized fraction of rice bran or rice bran oil. Such formulations also comprise a fortification agent, including, but not limited to, glucosamine derivatives (such as n-acetyl glucosamine, glucosamine sulfate), methylsulfonylmethane, and yucca concentrate. Additives to improve flavor and consistency of the product are also included in the formulation. Especially preferred formulations and dosages are described in Example 2.

B. Pharmaceutical Compositions

In other preferred embodiments, formulations of this invention are pharmaceutical compositions suitable for administration via various routes, preferably orally or topically, and for therapeutic and/or prophylactic administration. A number of suitable formulations for use in the present invention are found in Remington's Pharmaceutical Sciences (Mack Publishing Company, Philadelphia, Pa., 17th ed., 1985) and in *Dermatological Formulations: Percutaneous absorption*, Barry (Ed.), Marcel Dekker Inc., 1983, both incorporated herein by reference. Moreover, for a brief review of methods for drug delivery, see Langer, *Science* 249:1527–1533, 1990, which is also incorporated herein by reference. The pharmaceutical compositions described herein can be manufactured in a manner that is known to those of skill in the art, i.e., by means of conventional mixing, dissolving, levigating, emulsifying, encapsulating, entrapping or lyophilizing processes. It will be appreciated that the present methods and excipients are merely exemplary and are in no way limiting.

1. Topical Administration

More particularly, these compounds can be formulated into preparations in solid, semi-solid, or liquid forms suitable for local or topical administration, such as gels, water soluble (e.g., K-Y) jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities, such as K-Y jelly, are capable of providing an area with a prolonged exposure to the active ingredients. In contrast, a solution formulation provides more immediate exposure of the active ingredient to the chosen area, although the effects generally do not last as long.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation. Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, ORGELASE, water, calcium carbonate, calcium phosphate, various sugars, starches, cellulose derivatives, gelatin, and polymers such as polyethylene glycols.

2. Oral Administration

For enteral administration the compounds useful in the methods of the invention can be administered in either single or multiple dosages. The compounds may be administered in combination with pharmaceutically acceptable carriers in a variety of dosage forms. For example, capsules, lozenges, hard candies, powders, sprays, aqueous suspensions, elixirs, syrups, and the like may be formulated with various pharmaceutically acceptable inert carriers. Such carriers include solid diluents or fillers, sterile aqueous media and various non-toxic organic solvents.

Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

3. Dosages

Pharmaceutical compositions suitable for use in the present methods include compositions wherein the active ingredients are contained in a therapeutically or prophylactically effective amount. The amount of compound or composition administered will, of course, be dependent on the subject being treated, on the subject's weight, the severity of the affliction, and the manner of administration. A typical dosage for enteral administration is an amount from about 2 grams to about 100 grams per day. Determination of an effective amount is well within the capability of those skilled in the art, especially in light of the disclosure provided supra.

As used herein, "effective amount," or "therapeutically effective amount" refers to an amount of any of the compounds or formulations used in methods of the present invention that results in treatment of the medical condition, i.e., reduction in pain, redness, inflammation, lameness, or any other symptom. Alternatively, an "effective amount" may be determined by monitoring reduction in any detectable symptom of the condition, such as the degree of swelling, inflammation, redness, size of the affected area, range of motion, and the like. In the context of the present invention, "prophylactically effective amount" refers to an amount of any of the present compounds that prevents the development or relapse of a medical condition. For example, a "prophylactically effective amount" is an amount that protects a subject from developing an inflammatory disorder of the joint.

For any compound or formulation used in a method of the invention, a therapeutically effective dose can be estimated initially from animal models (described supra), well known to those of skill in the art. Such information can be used to more accurately determine useful doses in humans. Initial dosages can also be estimated from in vitro or in vivo data.

Initial dosages can also be formulated by comparing the effectiveness of the compounds used in the methods of the present invention in model assays with the effectiveness of known compounds. For instance, initial dosages can be formulated by comparing the effectiveness of the compounds in model assays with the effectiveness of other compounds that have shown efficacy in treating the present conditions. In this method, an initial dosage can be obtained by multiplying the ratio of effective concentrations obtained in the model assay for the compounds used in methods of the present invention and the control compound by the effective dosage of the control compound. For example, if a compound useful in a present method is twice as effective in a model assay as a known compound (i.e., the EC50 of the compound is equal to one-half the EC50 of the known compound in the same assay), an initial effective dosage of the compound would be one-half the known dosage for the known compound. Using these initial guidelines one having ordinary skill in the art could readily determine an effective dosage in humans or other mammals.

Dosage amount and interval may be adjusted individually to provide levels of the active compound which are sufficient to maintain therapeutic effect. One having skill in the art will be able to optimize therapeutically effective local dosages without undue experimentation.

4. Combination with Other Anti-inflammatory Agents

In pharmaceutical dosage forms, the present methods can use formulations where compounds are administered in the form of their pharmaceutically acceptable salts, or they may also be used alone or in appropriate association, as well as in combination with other pharmaceutically active compounds. Agents of particular use in the formulations of the present invention include, for example, local anesthetics, counterirritants, anti-inflammatory agents, or any agent that has a therapeutic effect for inflammatory diseases or conditions.

The preferred anti-inflammatory agents include, but are not limited to, prescription and nonprescription topical and aerosol corticosteroids, non-steroidal anti-inflammatory agents including salicylates, colchicine, para-aminophenols, propionic acids, macrolide immunosuppressives, dapsone, clobetasol, halobetasol, diflorasone, piroxicam, ketorolac, ketoprofen, indomethacin and specific cyclooxygenase inhibitors.

The preferred counterirritants include, but are not limited to, glycerol, corticosteroids and salicylates. The preferred anesthetics include, but are not limited to, amide caines and counterirritants with lidocaine, cocaine, bupivicaine, mepivicaine, etidocaine, chloroprocaine, proparacaine, tetracaine, benzacaine, prilocaine, benoxinate, dibucaine, dyclonine, pramoxine, menthol, resorcinol, thymol and camphor.

Any other compound that has potential efficacy in the treatment of the present conditions can also be used.

5. Routes of Administration

The compositions useful in the present methods can be administered to a patient using a variety of routes, such as oral, parenteral or local routes. The present compositions are typically administered to a patient as a local application, where "local application," or "locally applied," refers to the administration of a composition at the local site of the disease, whether by local injection, topical administration, or any such method that results in a relatively high concentration of the compounds used in methods of the present invention at the site of the disease. As such, administration of the compounds can be achieved in various ways, including by topical application of the composition to the site of the disease or condition, i.e., direct application of a formulation to the affected skin or mucous membrane. In addition, compositions can be formulated for injection and injected locally at the site of the disease or condition, e.g., local subcutaneous injection at the site of the disease.

6. Areas for Topical Application

The compositions useful in the present methods can be applied to any site of any of the present conditions, including localized conditions or conditions affecting large areas of the body or even covering the entire body, can be applied to the skin and/or to mucous membranes, and can be applied to any affected part of the body, including the face, forehead, chin, eyes, eyelids, eyebrows, nose, skin near the nose, cheeks, ears, mouth, tongue, inside of the cheeks, gums, head, hair, scalp, neck, chest, back, lower back, armpit, skin folds of armpit, elbow, elbow fold, wrists, ankles, legs, arms, insides of wrists, insides of arms, nails, knees, area behind knees, hands, feet, palms, soles, fingers, toes, genitals, or any other affected part of the body.

7. Frequency of Administration

The compositions useful in the present methods can be administered one time or multiple times, depending on the compound, the severity of the condition, and the initial response of the condition to the treatment. For example, the compositions can be administered 1, 2, 4, or more times per day, and can be administered every 1, 2, 4, 7, or more days. Such treatments can be administered for a limited duration, or indefinitely until the condition has resolved. The compositions can be applied locally as a "leave on" product, meaning that the composition is applied to the patient and allowed to remain indefinitely at the site of application, or as a "wash off" product, meaning that the composition is allowed to remain at the site of application for a limited amount of time, e.g., for a certain number of seconds, minutes, hours, etc.

It will be appreciated that the present methods of treatment can be applied alone or in combination with other surgical or non-surgical treatments for these conditions.

IV. Therapeutic Applications

As discussed previously, the formulations and methods of the invention are useful for treating inflammatory diseases or reactions. Preferably, these inflammatory diseases are disorders of the bone joint. In especially preferred embodiments, these methods are used to treat inflammatory diseases such as osteoarthritis, osteoporosis, rheumatoid arthritis, and soft tissue rheumatism. The term "treatment" is used to refer to a reduction of any of the symptoms associated with these inflammatory conditions, including, but not limited to, inflammation, redness, pain, swelling, lameness, and loss of mobility.

The methods of the present invention can also be used to prevent and/or treat inflammatory skin diseases (e.g., atopic dermatitis, eczema, contact dermatitis, allergic dermatitis), skin irritation, inflammatory pulmonary disease or reactions (e.g., asthma, allergic rhinitis, chronic obstructive pulmonary disease, and adult respiratory distress syndrome), inflammatory musculoskeletal disease or reaction (e.g., soft tissue rheumatism, exercise-induced injury, rheumatoid arthritis, psoriatic arthritis, osteoporosis and osteoarthritis), inflammatory gastrointestinal disease or urogenital reaction (e.g., enterocolitis, gastritis, Crohn's disease, interstitial cystitis, vaginitis, and ulcerative colitis), autoimmune disease or reactions (e.g., inflammatory bowel disease, and psoriasis), and transplantation rejection reactions.

Furthermore, the compounds of the invention can be used to treat lameness or loss of mobility arising from the inflammatory musculoskeletal diseases described above, as well as other conditions. In another preferred embodiment, the methods of this invention are used to treat pain in or around a bone joint arising from the inflammatory musculoskeletal diseases described above, as well as other conditions.

EXAMPLES

The following examples are offered to illustrate, but not to limit the claimed invention.

Example 1

This example illustrates the effectiveness of fortified formulations of stabilized rice bran derivatives for reducing lameness and joint inflammation in horses.

Figure 2:
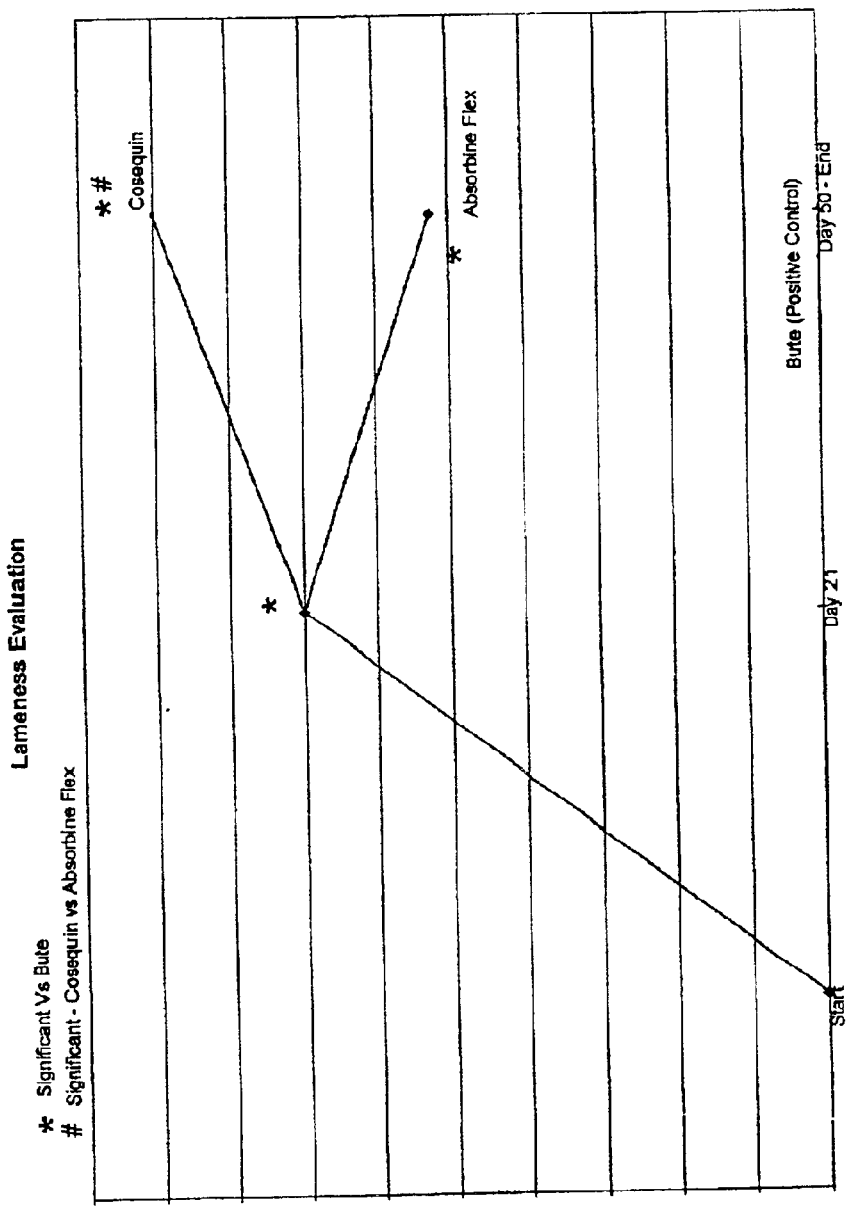
FIG. 2 illustrates the effect of formulations used in methods of this invention versus other commercially available treatments/NSAIDs on lameness of horses. The graph measures soundness score (measurement of lameness) after treatment with "bute", Cosequin, Absorbine Flex over 50 days.
Figure 3:
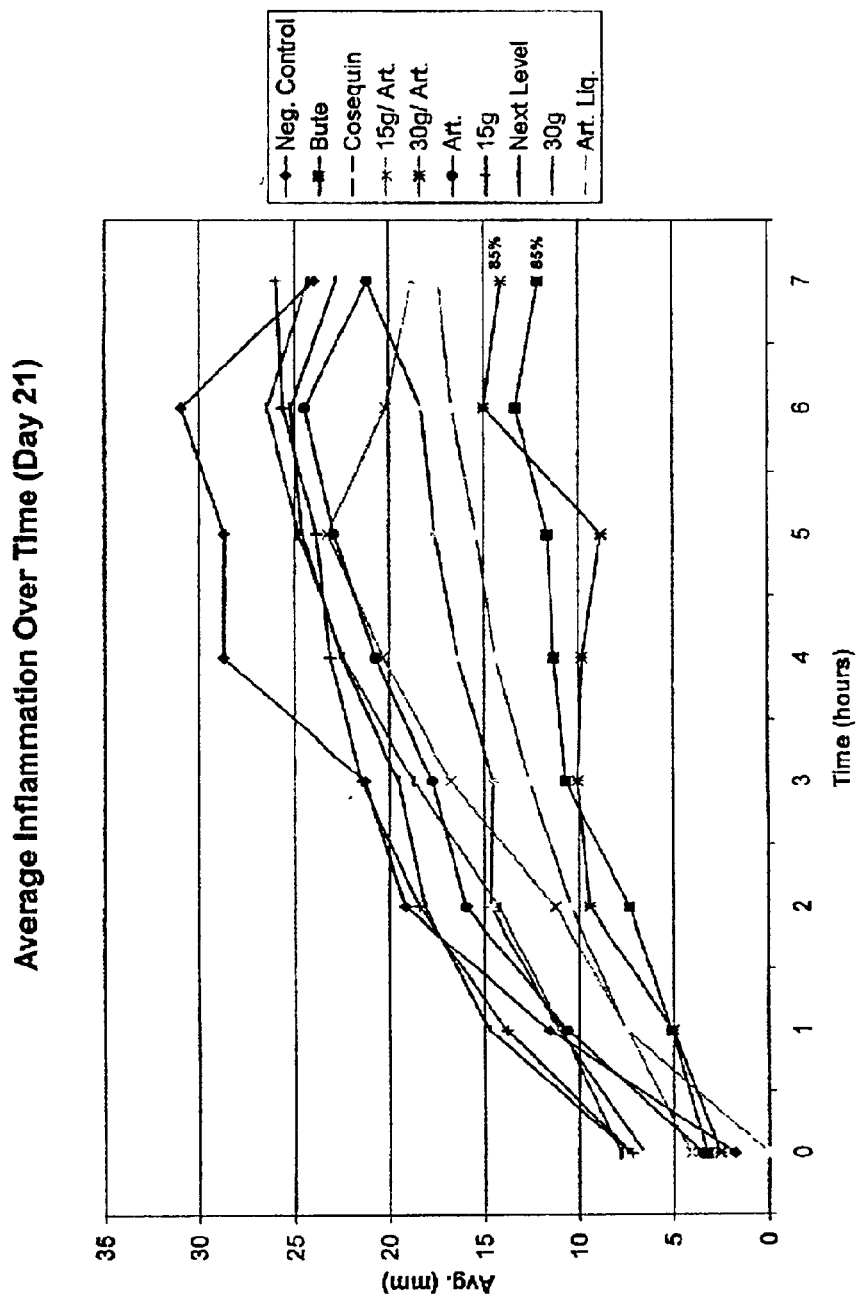
FIG. 3 illustrates the effect of treatment with formulations of this invention versus other commercially available nutraceuticals/NSAIDs on levels of carrageenan-induced inflammation on Day 21 of the clinical trial. Injection is induced and then the size of inflammation at the site of injection with carrageenan is measured over 7 hours for horses treated with the negative control, "bute", Cosequin, Next Level, or Absorbine Flex.
Figure 4:
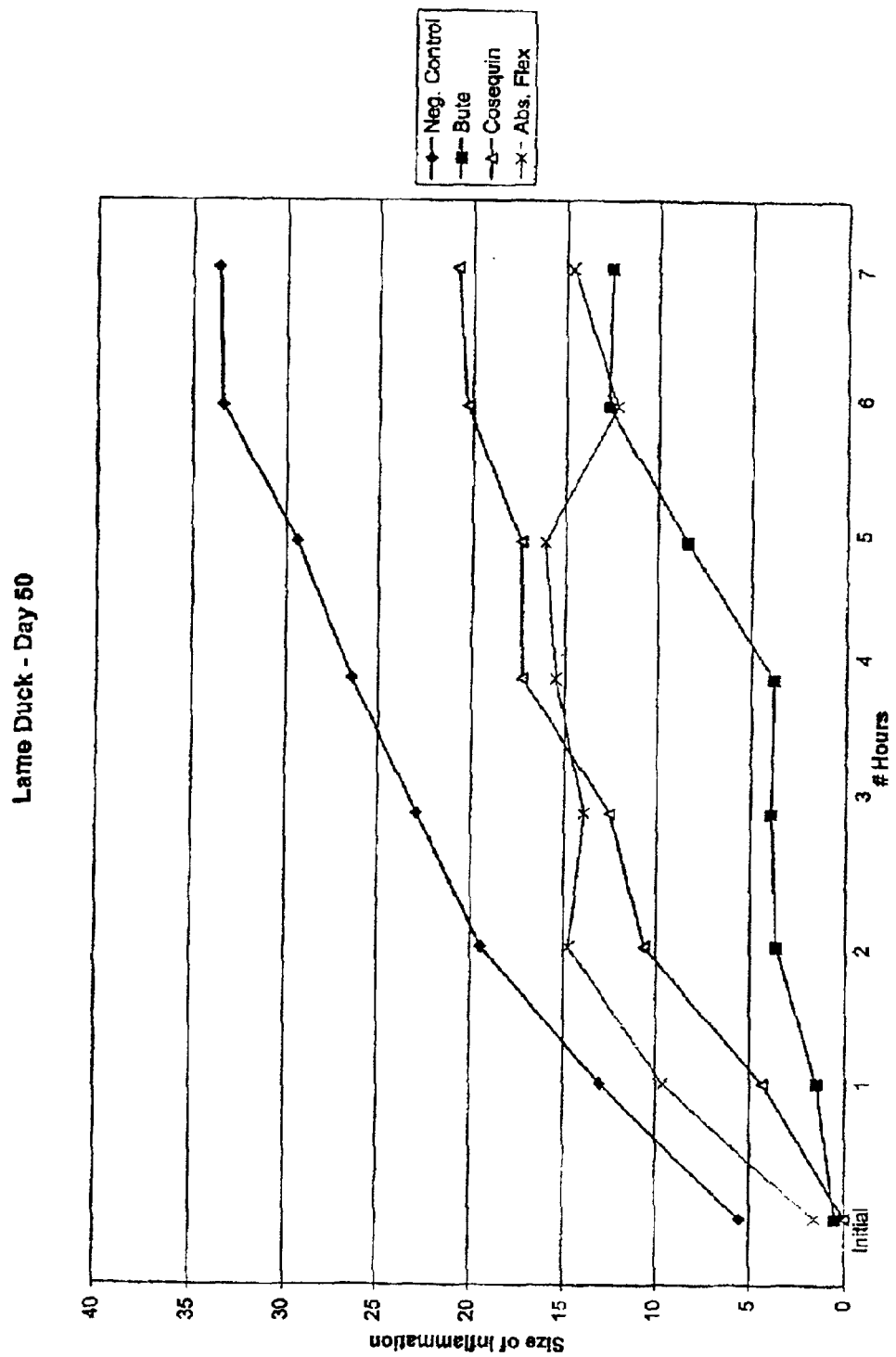
FIG. 4 illustrates the effect of treatment with formulations of this invention versus other commercially available nutraceuticals/NSAIDs on levels of carrageenan-induced inflammation on Day 50 of the clinical trial.

Clinical trials on 51 horses were conducted to determine the ability of formulations of this invention to improve lameness and reduce joint inflammation. Horses were fed with formulations of this invention and other commercially available treatments used to treat lameness. Horses were videotaped on day 1, day 21, and day 50 of the trial. Lameness was evaluated using the scoring system illustrated in FIG. 1. The correlation between treatment with the various formulations and "lameness" is illustrated in FIG. 2. The effect of treatment with the various formulations on inflammation was measured by injecting the neck of the horse with carrageenan on day 21 and day 50, then observing the size of the injection site over 7 hours (FIG. 3). Prior to initiation of the trial, a range-finding study was conducted to determine the amount of carageenan and route of administration necessary to induce measurable amounts of inflammation.

A range finding study was conducted to find quantifiable endpoint of carrageenan induced subcutaneous skin inflammation and to compare various commercially available oral products designed to reduce inflammation in horses and to then compare these to phenylbutazone administration intravenously 12 hours prior to comparison and again one hour to commencement of comparison, on day 21 and day 50 post commencement feeding of the oral preparations. A 0.1 mL of subcutaneous injection of 2% carrageenan in sterile water, autoclaved for sterility provided a reproducible challenge under the study conditions utilized. A dose of 2 grams of phenylbutazone given intravenously twice prior to each evaluation (lay provided by a clinically significant reduction in inflammation for comparison.

Preparation of potential horses for the project consisted of evaluation of general health and history of clinical health and soundness. Where pertinent, a routine lameness evaluation to verify presence of arthritic and/or lameness of long-standing duration rather that short-term lameness (bruises, soft tissue damage, etc.) that would heal with or without intervention. If an individual satisfied these criteria, then routine immunizations (tetanus toxoid, eastern-western encephalitis influenza, and rhino-pneumonitis) as well as cost to the owners. Once the trial cell was completed, containing three of five clinically lame horses (exception trials cells "A" and "B"), then each individual was given a project number for identification. Each number was then branded into the antero-lateral aspect of the hoof was on the left front hoof for identify verification on days #1, day #21 and day #50.

Fifty one horses (10 groups of 5 each with one extra) were fed a basal diet consisting of alfalfa and/or grass hay, oats and stabilized rice bran as needed for consumption of the various oral products being evaluated. Horses were not randomly selected for the trial cells, since at least three of five in each cell had to exhibit clinical lameness. (Cells "A" and "B" excluded from this requirement) Horses once identified as a part of the trial were eliminated if (1) they refused to eat the product (2) were given medication other than those included in the project, for whatever reason that might interfere with the results.

The purpose of this study was to compare the various products, both available and non-available, alone or in combination with each other and against phenylbutazone, the "benchmark" NSAID for tissue inflammation reductions. In addition, videos of lame horses were taken on day #1, #21, and #50 for subjective evaluation. Looking for improvement in the lameness condition presented on day #1.

A. Materials and Methods

A range finding study was conducted to find quantifiable endpoint of carrageenan-induced subcutaneous skin inflammation and to compare various nutraceutical products both commercially available and yet-to-be available to phenylbutazone, the "benchmark" anti-inflammatory drug in equine veterinary medicine.

In determining a quantifiable endpoint for carrageean injection 200 mL of a 2% w/v sterile preparation was made by certified compounding pharmacist, using autoclave method for final sterilization. Six horses were chosen for initial evaluation of the product. An area approximately 8 cm×24 cm was clipped on the side of the neck mid-cervical and approx. 3 cm below the mane and upon whichever side the mane flows. The area was scrubbed with 70% alcohol-essential oil skin preparation. Immediately six small dots were placed using waterproof marker in the clipped area approximately equidistant horizontally along a line tuberculosis syringe using a 25 gauge ⅝" needle inserted through the rubber stopper previously saturated with 70% alcohol and allowed to partially dry. In addition, 0.2 mL. increment of 2% carrageean (w/v) was drawn into 5 subsequent tuberculosis syringes and hub could thus be accounted. Animal was then retrained and a 0.1 cc increment was then placed intradermally under each skin mark, starting the 25 gauge ⅝" needle approximately 3⁄16" from the mark in a scrubbed area and ending with the point of the needle under the indelible mark. No surgical gloves were used, but care was taken to avoid post-scrub skin contamination. All six horses were injected intradermally as described for dogs in the canine DCV project. Four of the six horses exhibited inflammatory lumps of 12×16 mm to 18×22 mm in size which enlarged in an elliptical fashion initially within 2–3 hours, but did not regress measurably past the initial size even after several weeks. The lumps seemed to be mildly to moderately tender with the horses apprehensive when even slight digital pressure applied to the test area. The initial swelling induced by the sterile water approximated the carrageean swellings, but regressed to near and normal within several hours. Since the swellings induced did not fit the trial protocol requirement s, a second route of administration was performed on 6 different horses. In the second group of range findings study horses, only route of administration changed. All 0.1 cc injections were placed subcutaneously rather intradermally. Restraint again was important as any carrageenan laced along the route of administration upon needle withdrawal tended to induce a lingering blob as well as initial measurable swelling post injection at the sire of needle induction. In some instances this was unavoidable under best of circumstances and restraint due to normal equine response to needle penetration and material placement under the cutaneous later of skin. In other instances, some micro bleeding at injection site was unavoidable and apparent. In each case, swelling was measured and recorded, since micro bleeding tends to resolve within several hours and certainly in less than 5 hours in each instance.

Swelling resulting from subcutaneous placement of 2% carrageenan were mostly elliptical, measurable, and transient. Sites ranged from 0 mm×0 mm, initially to 45 mm×60 mm after 7 hours.

After 14 days post range finding evaluation, three of the six horses initially used were then chosen at random, administered intravenous phenylbutazone at 1.0 gms. Per 500 pounds body weight and again challenged with 0.1 cc of 2% carrageenan in five sites, using 0.1 cc sterile water as a control. All injections were given subcutaneously as previously described. Size of resulting lumps was measured immediately and again at hourly intervals for 7 hours. Resulting swellings were minimal, measurable, and provided a comparison to phenylbutazone given at the recommended dose and frequency generally used. Note however that phenylbutzone cannot be used on a race day at racetracks sanctioned for public wagering. In addition AHSA (American Horse Association) sanctioned shows have specific guidelines which specify when and how much phenylbutazone may be administered to a competing horse. This initial evaluation as well as follow-up evaluation during the test trials suggests the benefits of phenylbutazone as it may be used to satisfy drug-testing policy may be long gone prior to competition. This makes the benefits derived from oral nutraceuticals all the more important and meaningful in controlling inflammation. The transitory nature of phenylbutazone benefit when used under present guidelines places it more in the "band aid therapy" category than previously recognized by veterinarians and horsemen alike. Nevertheless it will remain as the standard by which most responses to inflammation/lameness treatments are measured likely for years to come.

Fifty-one horses were selected for ten treatment groups. Horses picked were selected at random for age, use, breeding, weight and sex. Age ranged from 1 year to 37 years of age. Use included retired, broodmares, herd sires, western performance, hunter-jumper performance, in early training, and untrained. Breeding included quarter horse and quarter horse cross, thoroughbred cross, appaloosa, and paints. Weight varied from approximately 700 lbs to 1200 lbs. There were 7 intact males, 27 castrated males, and 17 intact females. Horses were housed under typical upper-scale horse facilities in two climates with 26 head in northwestern Montana and 25 head in central Ariz., USA. Ambient temperatures during the trial period ranged from 5 F to 106 F. All the products were stored at 73 F to 82 F and fed at ambient temperatures. All attempt was made to utilize horses typical of those eventually targeted for the product being evaluated, and under conditions typically seen when products comes to market.

3.8 Justification for route of administration: The test product is intended to be administered as a supplement to the basal diet.

3.9 Acclimation: All animals were acclimated for at least 2 weeks prior to the study.

3.10 Selection Criteria

| Treatment Group | Animals | PL-100 | Equiflex fed. A. | Glucosamine b. | Phenylbut. admin. c. | Carageen. admin. |
|---|---|---|---|---|---|---|
| A | 5 | NO | NO | NO | NO | YES |
| B | 5 | NO | NO | NO | YES | YES |
| C | 5 | NO | NO | COSEQUIN | NO | YES |
| D | 5 | NO | NO | NEXT LEVEL | NO | YES |
| E | 5 | 15 gm/day | YES | YES | NO | YES |
| F | 5 | 15 gm/day | YES | YES | NO | YES |
| G | 5 | 30 gm/day | YES | YES | NO | YES |
| H | 5 | 30 gm/day | NO | YES | NO | YES |
| I | 5 | NO | YES | YES | NO | YES |
| J | 5 | NO | YES liquid only | YES | NO | YES |

A. loading dose will be double dose for 21 days maintenance dose will be single dose for 30 days
b. Cosequin and next level given at <u>maximum</u> recommended dose
c. Phenylbutazone given at 1 gm/500 lbs 12 hours prior to challenge and 1 gm/500 lbs 1 hour prior to challenge with carrageean Cells to contain minimum of 3 clinically lame horses with the exception of cells "A" and "B".

Fifty-one horses were selected for ten treatment groups. Horses picked were selected at random for age, use, breeding, weight and sex. Age ranged from 1 year to 37 years of age. Use included retired, broodmares, herd sires, western performance, hunter-jumper performance, in early training, and untrained. Breeding included quarter horse and quarter horse cross, thoroughbred cross, appaloosa, and paints. Weight varied from approximately 700 lbs to 1200 lbs. There were 7 intact males, 27 castrated males, and 17 intact females. Horses were housed under typical upper-scale horse facilities in two climates with 26 head in northwestern Montana and 25 head in central Arizona, USA.

B. Purpose of the Study 1.0 A study conducted by White Eagle Toxicology Laboratories in Doylestown, Pa. Under direction of DVC Biologics, L.P. of Wilmington, Del. described the effect of egg powder on acute carrageean-induced inflammation in female beagle dogs. Findings indicated a significant reduction in inflammation. The purpose of this study was to compare reduction in inflammation induced by carrageean resulting from various commercial nutraceuticals claiming inflammation reduction with egg powder and egg powder and Equiflex combinations using Phenylbutazone as a benchmark comparison anti-inflammatory in the horse.

2.0 Study Schedule

Study initial date—July, 2000 Experimental termination—November, 2000

3.0 Test System:

3.1 Species: Horse
Breed: Qrt, Qrtx, Qrt-tbx, Appaloosa, Paint
3.2 Supplier: Randy Johnson Qrt Horses Diamond B Ranch Mark ArnoldGary D. Kaufman, D. V. M Scott Davis
3.3 Age: 1 year to 37 year
3.4 Number:51
3.6 Justification for test system selection: Horses in use in typical life-style of those anticipated as target group for commercial product.
3.7 Justification for the number of animals: This study was designed to use the fewest number of horses possible consistent with the objective of the study and scientific needs.

All the horses were evaluated for general health and lameness if present. Horses were selected if they healthy, not likely to require medication for the next two months, and at least exhibit lameness from chronic rather than acute inflammatory changes.

4.0 Animal Husbandry:

4.1 Housing: Horses were housed in individual stalls, runs, pastures, or combination three.
4.2 Environmental conditions: The horses maintained according to currently acceptable practices of good animal husbandry.
4.3 Food: Alfalfa and/or grass hay with/without oats and supplemented with a stabilized rice bran as needed to consume test product.
4.4 Water: Available ad libitum
4.5 Non contaminants were known to be in the feed or water that would be expected to alter to outcome of the study.

5. Animal Identification and Randomization:

Each horse was individually identified using a hoof brand number burned into the anterolateral aspect of the left front hoof. Horses for each treatment group were not randomly assigned since three of 5 in groups "C" through "J" required a clinical lameness 6.0 Test products:

6.1 Identity: Egg powder, "Cosequin", "Next Level", and Equiflex.
6.2 Source of test product: Wolcott Farms, RiceX, DVC Biologics, Nutramax Laboratories & Sure Nutrition.
6.3 Storage conditions/stability: Test products were stored at room temperatures in a dry place protected from sunlight. Stability of the products under conditions of storage as stated.
6.4 Disposition of the test products: At the conclusion of this study all unused portions are being held or disposed of as directed by study director.

7.0 Study Design 7.1 Range finding study: A range finding study was conducted to: (1) establish a measurable carrageenan induced inflammation on the neck under the mane and (2) to verify that phenylbutazone given in an accepted manner would significantly reduce inflammation caused by carrageenan to use as a comparison.

During attempts to establish a measurable carrageenan induced inflammation using route of administration suggested by DCV Biologics. Multiple attempts were unsuccessful. Inflammation did not show a patterned increase in size of bleb and transitory swelling suggested. Rather it result in a small painful lump that frequently did not increase nor dissipate in any set pattern, but rather lingered for weeks and sometimes months as a painful, obvious swelling.

A second model was evaluated using subcutaneous route of administration with all other parameters being identical. A transitory lump was produced with almost all evidence being gone in 24–40 hours. In addition, the swellings were quite measurable over 7 hour period, increasing and in some instances starting to decrease within that time frame.

The swellings were for the most part elliptical or at least not perfectly round. Inflammation in horse skin id often manifest in a rash" appearance rather than round lumps, so the shape of swelling was of no real surprise. Measurements were taken using basically height×width of the swellings to establish a more representative number to describe the reaction to the carrageenan-induced inflammation. It should be noted that swelling is a 3 dimensional phenomenon as each lump had thickness as well as height and width. In some horses, measurements went from a significant width× height to 0x0. In these cases the swelling melted away first in the middle of the lump and eventually dissipated at the borders to the extent no readings were possible. This again is not surprising, since skin swellings in horses often vanish in this manner. Strictly reading the numbers in these cases may be quite confusing. In this trial, swellings were simply identified, measured and numbered and when identification was no longer possible, measure was called 0×0.

7.2 Efficacy study of the tests products: Al tests products were measured using and electronic gram scale for solids and graduated dose syringe for liquids. Each product was measured and a daily amount was measured was placed in an individual plastic container and heat-sealed using a Food saver Bag Vac Sealer. All liquids were placed in a bag within a bag and heat-sealed. Each bag was then labeled with the horse's name and identification number. Each product was mixed as requested under protocol treatment chart. Only the product to be given from day 1 to day 21 was issued to complete the trial. Treatment group "J" did not receive daily liquid Equiflex after day 21 challenge simply because product did not arrive form Rice-X as requested in a timely fashion. Upon arrival, product was fed as a loading dose for 6 days to compensate and ultimately allow for total amount of product in the horses by day 51. This variance was discussed with and approved by Win of Wolcott Farms as the logical correction to make. Cosequin was fed twice daily three level scoops each time. This was continued throughout the entire 51 days rather than drop to maintenance dose, since the label suggests that the horse should be watched for "movement and attitude" and that maintenance or transitional dosage of a lesser amount "may be increased at any time if needed". Rather than get it an issue, since comparisons get into an issue, since comparisons were being drawn, Cosequin was fed throughout at maximum recommended dose. Next level was fed at maximum dose of 2 oz throughout the first 21 days rather than the first 10 days, and then dropping to 1 oz per day as the label suggests. Again this was to ensure maximum results. Egg biologics was fed at 15 gm/day and 30 gm/day. Each was doubled during the first 21 days. When used in combination with equiflex/glucosamine both egg biologics and equiflex/glucosamine were doubled in amount. Equiflex was fed at a dose of 2.75 oz as a standard dose and a 2.72 oz when fed with egg biologics. Liquid Equiflex was fed 4.25 oz/day maintenance, 8.5 oz/day loading dose.

8.0 Antemortem Observations 8.1 Local observations: Each animal was observed at least twice a day during feeding time and any changes noted. #59 Bowie was eliminated from the trials after day #5 for refusal to eat the loading dose of 60 gms/day egg biologics with 5.44 oz day Equiflex powder. #7 Dolly was given intravenous flunixamine on day 20 and scratched from the day 21 evaluation, but included in the day 50 evaluation. #1 Copper was eliminated from the trial after carrageenan included lumps persisted on his neck for more than two weeks post-injection. #18 Mercedes was eliminated on day 23. He required continuous medication for gastric ulcers, which could potentially alter trial results.

8.2 Data collection: All measurements were taken by the study director and recorded by support personnel. Measurements were made hourly for 7 hours with most being on the hour with few varying several minutes, depending on the difficulty experienced in restraining fractious/dangerous animals.

| | | |
|---|---|---|
| TITLE: | Evaluation Of The Anti-Inflammatory Efficacy Of PL-100 (a whole egg product, ex DCV), 'Arthreflex', 'Next Level' and 'Cosequin' on Horses versus 'Bute' | |
| PURPOSE: | Assess the statistical and clinical efficacy of two test products (PL-100 in an inert carrier base and in combination with 'Arthreflex') versus three market controls in i) an equine model of inflammation, and ii) clinically lame horses. | |
| ANIMALS: | SPECIES: | Equine |
| | STRAIN/BREED: | Variety - To be |
| | SEX: | documented |
| | AGE: | To be |
| | SOURCE: | documented |
| | | 3mo - 25 years |
| | Method of IDENTIFICATION: | to be documented |
| | Total NUMBER: | |
| | Treatments: | |
| | Number per TEST GROUP: | |
| | Number of REPLICATES: | 50 |
| | | 10 |
| | | 5 horses per |

-continued

|  |  |  | treatment 1 |
|---|---|---|---|
|  | Type and description of HOUSING: |  | Stabled horses |
|  | Husbandry, vaccinations, general management: |  | All horses are immunized according to local standard prior to starting |
| RATION/ DIET: | BASAL DIETS Source: |  | Alfalfa roughage diet with additional grain |
|  | Nutrient Specifications: |  | Protein 14% - 20% Basal diets are based upon NRC |
|  | Formula: |  | Nutritionally adequate and on that is commonly utilized for feeding the type of horse used in the trial. |
|  | Medication: |  | None |
| EXPERIMENTAL DESIGN: | Total # Horses: |  | 50 |
|  | Total # Males/Females: |  | random |
|  | Total # Treatment Groups: |  | 10 |
|  | Total Duration of Treatment: |  | 50 days |
|  | Method of Randomization: |  | To be documented |
|  | Blinding: |  | None |
|  | Statistical Analysis: |  | Student's t-test, ANOVA & Bonferroni's Multiple Comparison post-test. |

TREATMENT GROUPS:

| Treatment Group | #'s Animals | PL-100 Fed[a] | Arthreflex | Glucosamine[b] | Phenylbutazone Administered[c] | Carrageenan Administered |
|---|---|---|---|---|---|---|
| A | 5 | No | No | No | No | Yes |
| B | 5 | No | No | No | Yes | Yes |
| C* | 5 | No | No | Cosequin | No | Yes |
| D* | 5 | No | No | Next Level | No | Yes |
| E* | 5 | 15 gm/day | Yes | Yes | No | Yes |
| F* | 5 | 15 gm/day | No | Yes | No | Yes |
| G* | 5 | 30 gm/day | Yes | Yes | No | Yes |
| H* | 5 | 30 gm/day | No | Yes | No | Yes |
| I* | 5 | No | Yes | Yes | No | Yes |
| J* | 5 | No | Equiflex Liq | Yes | No | Yes |

[a]Loading dose will be bid for 21 days Maintenance dose will be sid for 30 days
[b]1800 mg twice a day
[c]to be documented
*Cells to contain minimum of 3 Clinically Lame Horses Experimental Design:

Rangefinding Study: A rangefinding study was conducted to establish a quantifiable end point of carrageenan induced inflammation and to determine the dose of phenylbutazone which will reduce the inflammation by approximately 50%. Based on these results, the procedure for challenge will be as follows:

An area on the body will be clipped and six small lines will be drawn on the neck with marker. Five (5) 0.1 mL intradermal injections of 2% carrageenan in sterile water will be made in the clipped area and a single injection of water will serve as a control. The diameter of the injection sites will be measured with calipers and recorded immediately after injection and hourly there after for 7 hours following injection. 5 test sites and 1 control (water) per horse, therefore 25 test sites per test cell+5 controls All PL-100/Glucosamine treatments will be mixed by DuCoa prior to application and shipped to the test facility. Retention samples of PL-100 will be retained for assay by DCV. Retention samples for all products will be retained for assay by WFY. Prior to initialization of the trial, horses will be selected the basis of comparable size and general good health. Animals will be grouped by treatment as described in the treatment table above. Horses given PL-100 will receive a loading dose (defined as the maintenance dose given twice a day) for 21 days. Horses on market control products will follow manufacturer's instructions. On day 21 all horses will be challenged with carrageenan and evaluated for inflammatory response. Ideally, the same person should do the intradermal injections and the same person should do the measuring of the inflammatory response. Starting on day 22, the horses receiving PL-100 will be given PL-100 once a day as a maintenance dose. All horses will then be challenged with carrageenan on day 50

Clinically Lame Horses—Observational Methods

Prior to the start of the trial each clinically lame horse will be exercised recorded by videotape. The video evidence should clearly illustrate the animals' stride, extension and general mobility. The same record of the animals' physical exhibit should also be kept at day 21 and day 50 of the trial. The performance difference should be evaluated across these three intervals by the same evaluator. The evaluators' comments and observations will be part of the trial record. The same evaluator should be used for each of the clinically lame horses.

| SCHEDULE: | Date | Treatments |
|---|---|---|
| | August (day 0) | House horses |
| | | Start trial feeding |
| | | Size test |
| | August (day 21) | Challenge horses |
| | September (day 50) | Measure results |
| DATA MEASUREMENTS & RECORDS: | Data Collected or Measurement | |
| | Record daily observations for general health and disease status throughout trial period | |
| | Record reasons for any removal of animals & specific exclusion criteria met | |
| | Record disposition of all animals and materials and attach receipts | |
| METHOD OF DATA ANALYSIS & STATISTICS: | Group mean values (+Std. Devns.). Pre- vs Post- comparisons within each treatment group conduct using paired Student's t-test. Between group comparisons using one-way ANOVA. Where significant differences ($p \leq 0.05$) are seen, use Bonferroni's Multiple Comparison post-test to determine which means are significantly different from each other. | |

Example 2

This example sets forth preferred formulations of this invention.

Human Formulations

NutraFlex ™ (For Humans)
Serving Dose 10 grams/day

| | |
|---|---|
| RiSoluble ™ | 79% ± 5 |
| Yucca | 10% ± 1 |
| Glucosamine Sulfate | 5% ± 1 |
| N-Acetylglucosamine | 3% ± 0.3 |
| Methylsulfonylmethane (MSM) | 2% ± 0.3 |
| Grape seed extract | 1% ± 0.3 |

NutraFlex: Drink

| | |
|---|---|
| NAG | 3% ± 0.5 |
| MSM | 2% ± 0.3 |
| Yucca | 10% ± 1 |
| Glucosamine Sulphate | 5% ± 1 |
| Grape seed ext | 1% ± 0.1 |
| Boswellin | 1% ± 0.1 |
| Solubles | 78% ± 5 |
| Dose | 10.0 g/day |

NutraFlex: Capsules

| | |
|---|---|
| RiSolubles | 28.0% ± 3 |
| N-Acetyl Glucosamine | 11.11% ± 1 |
| Glucosamine sulphate | 16.67% ± 2 |
| Methyl Sulfonyl Methane | 11.11% ± 2 |
| Grape seed extract | 5.58% ± 1 |
| Yucca Concentrate (70%) | 5.58% ± 1 |
| Hemp seed oil | 5.58% ± 1 |
| Boswellin | 5.58% ± 1 |
| Ginger powder | 5.58% ± 1 |
| Curcumin (95%) | 5.58% ± 1 |

Total 1.80 g for 4 capsules two with breakfast and two with dinner

-continued

NutraFlex: Bar

| | |
|---|---|
| Solubles | 48.39% ± 3 |
| N-Acetyl Glucosamine | 8.06% ± 2 |
| Glucosamine sulphate | 8.06% ± 2 |
| Methylsulfonylmethane | 16.13% ± 2 |
| Yucca concentrate | 3.23% ± 0.5 |
| Grape seed extract | 3.23% ± 0.5 |
| Aswagandha | 8.06% ± 0.7 |
| Ginger powder | 3.23% ± 0.5 |
| Curcumin | 1.61% ± 0.3 |

Formulations for Horses

EquiFlex ™ (For Horses)
Serving size 2.75 oz/day (78 grams/day)

| | |
|---|---|
| Stabilized Rice Bran | 88.47% ± 5 |
| Yucca | 5.13% ± 1 |
| Glucosamine Sulfate | 3.84% ± 0.5 |
| N-Acetylglucosamine | 1.28% ± 0.3 |
| Methylsulfonylmethane (MSM) | 1.28% ± 0.3 |
| Total | 100% |

EquiFlex-Liquid Formulation

| | |
|---|---|
| Rice Bran Oil | 30–60% |
| Glucosamine Sulphate | 2.62% ± 0.5 |
| N-Acetylglucosamine | 0.87% ± 0.2 |
| Methylsulfonylmethane | 0.87% ± 0.2 |
| Yucca Concentrate (70%) | 3.5% ± 0.3 |
| Water | 30–60% |
| Gum (Emulsifier) | 0.2% ± 0.05 |
| Sodium benzoate(Stabilizer) | 0.15% ± 0.03 |
| Citric acid (Preservative) | 0.6% ± 0.1 |
| Apple flavor | 0.25% ± 0.05 |
| Dose | 155 g/day |

Topical Formulations

Arthritis Cream

Distilled Water
EPA
Toco
Emu Oil
Stabilized Oxygen
Orange Oil
Silica
Colloidal Silver
Lemon Oil
Poly Base
Yucca
Glucosamine sulfate
Methylsulfonylmethane All publications, patents and patent applications mentioned in this specification are herein incorporated by reference into the specification in their entirety for all purposes. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method for treating lameness or loss of mobility in a mammal, said method comprising:
    administering a fortified formulation comprising a stabilized rice bran derivative and at least one fortification agent where in said fortification agent is a member selected from the group consisting of a glucosamine derivative, methylsulfonylinethane, yucca concentrate and grape seed extract, wherein said stabilized rice bran derivative is a member selected from the group consisting of rice bran oil, enzyme-treated stabilized rice bran where in the enzyme is carbohydrate cleaving enzyme, a stabilized rice bran solubilized fraction, and mixtures thereof, thereby treating lameness or increasing joint mobility.

2. The method of claim 1, wherein said administering comprises ingestion of said fortified formulation.

3. The method of claim 1, wherein said mammal is a human.

4. The method of claim 1, wherein said mammal is an animal.

5. The method of claim 4, wherein said animal is a member selected from the group consisting of a horse, a cat, and a dog.

6. The method of claim 1, wherein said formulation is ingested in the amount of about 2 grams to about 100 grams per day total.

7. The method of claim 1, wherein said formulation is a member selected from the group consisting of a cream, a capsule, a bar, a powder, a food, a food supplement, a medical food, a liquid, a beverage, an emulsion or mixture thereof.

8. A method for inhibiting prostaglandin synthetase activity, said method comprising:

administering a fortified formulation comprising a stabilized rice bran derivative and at least one fortification agent where in said fortification agent is a member selected from the group consisting of a glucosamine derivative, methylsulfonylinethane, yucca concentrate and grape seed extract, wherein said stabilized rice bran derivative is a member selected from the group consisting of rice bran oil, enzyme-treated stabilized rice bran where in the enzyme is carbohydrate cleaving enzyme, a stabilized rice bran solubilized fraction, and mixtures thereof, thereby inhibiting prostaglandin synthetase activity.

9. The method of claim 8, where said administering comprises ingestion of said fortified formulation.

10. The method of claim 8, wherein said formulation is ingested in the amount of about 2 grams to about 100 grams per day total.

11. The method of claim 8, wherein said formulation is a member selected from the group consisting of a cream, a capsule, a bar, a powder, a food, a food supplement, a medical food, a liquid, a beverage, an emulsion or mixture thereof.

* * * * *